United States Patent [19]

Loran et al.

[11] Patent Number: 4,941,826
[45] Date of Patent: Jul. 17, 1990

[54] APPARATUS FOR INDIRECT DENTAL MACHINING

[76] Inventors: William Loran, 100 Thorndale Dr., #356, San Rafael, Calif. 94903; Merritt A. Robinson, 475 Fawn Dr., San Anselmo, Calif. 94960

[21] Appl. No.: 204,632

[22] Filed: Jun. 9, 1988

[51] Int. Cl.⁵ .............................................. A61C 3/06
[52] U.S. Cl. ...................................... 433/51; 433/76; 433/215; 433/223
[58] Field of Search ....................... 433/25, 27, 51, 68, 433/75, 76, 114, 215, 223

[56] References Cited

U.S. PATENT DOCUMENTS

| | | | |
|---|---|---|---|
| 3,839,797 | 10/1974 | Randolph | 433/27 |
| 4,182,312 | 1/1980 | Mushabac | 433/68 |
| 4,411,626 | 10/1983 | Becker et al. | 433/223 |
| 4,478,580 | 10/1984 | Barrut | 433/223 |
| 4,575,805 | 3/1986 | Moermann et al. | 433/68 |

*Primary Examiner*—John J. Wilson
*Attorney, Agent, or Firm*—Melvin R. Stidham

[57] ABSTRACT

Apparatus for machining a human tooth includes a rotary cutter that is moved along a predetermined path dictated by motor energizing signals. The cutter is moved vertically by one drive, laterally by another drive and in or out by a third drive. The apparatus is clamped selectively to the patient's jaw or to a model thereof. The dentist's manual work is actually done on a model, with the apparatus being secured to the model in a fixed position. The vertical drive, the lateral drive, and the in or out drive are energized in response to the dentist's manipulation of a joy stick to move the cutter along paths necessary to achieve the desired tooth configuration. A second joy stick is manipulated to vary the attitude of the cutter, about roll and/or pitch axes. Signals proportionate to the extent of each drive operator are delivered to a computer in the sequence and for the period during which the drives are activated. When the machining is completed on the model, the restoration is prepared from the model, and the patient is then called back. The device is then secured to the patient's jaw so that it is in precisely the same relative position as on the model. Then, the computer delivers drive motors machine strokes in the proper sequence to duplicate the machining previously done on the model.

12 Claims, 4 Drawing Sheets

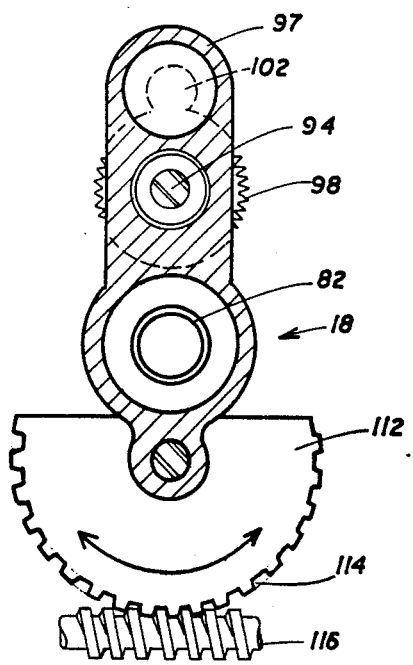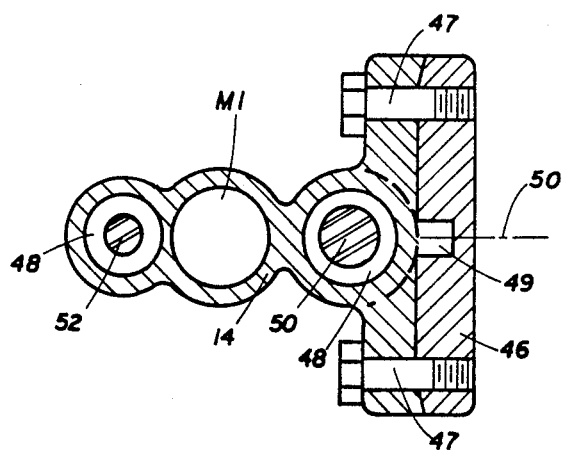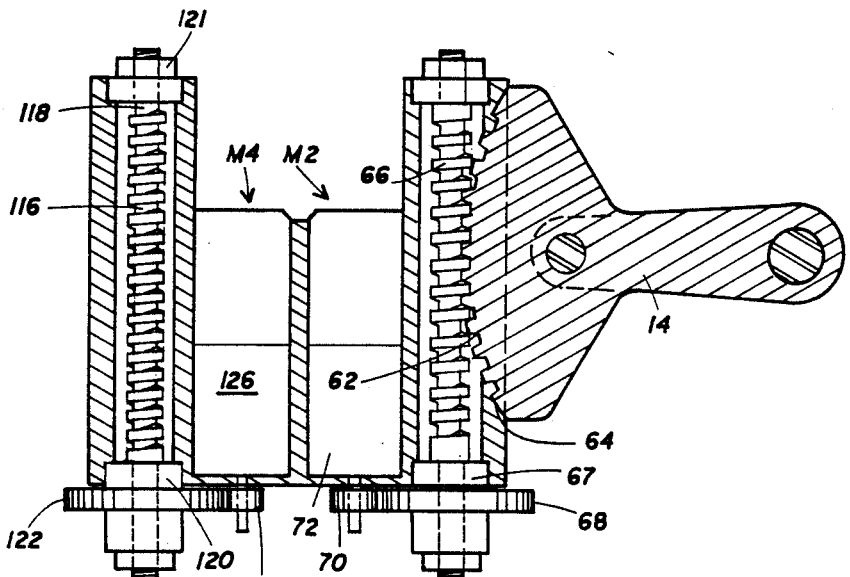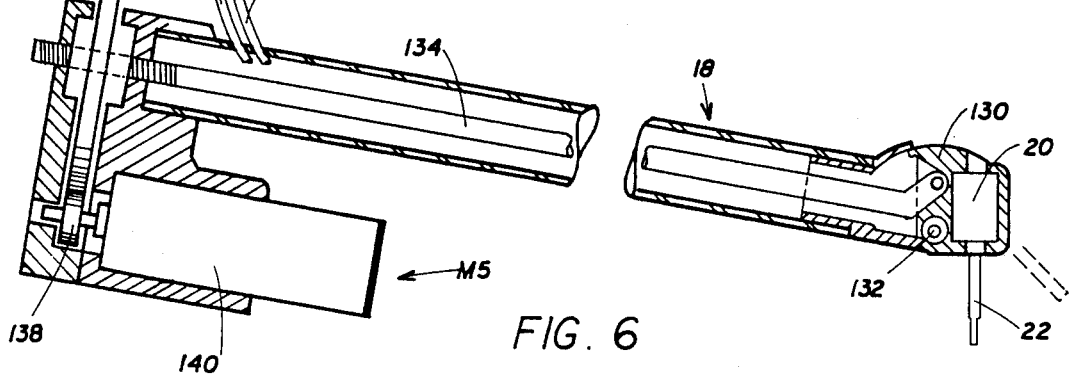

APPARATUS FOR INDIRECT DENTAL MACHINING

BACKGROUND OF THE INVENTION

This invention relates to an apparatus which enables the machining of teeth to be done indirectly. According to current, direct machining practice, when teeth are being prepared for restorations, they are cut by the dentist with a hand-held rotating cutter. The dentist must approach the work through the mouth opening and then must, of necessity, operate in the highly confined space of the patient's mouth wherein manipulation of the cutter is often restricted by other teeth, as well as by the patient's tongue and cheek. A mirror is required, not only to enable the dentist to observe the back of the work, but to restrain the tongue and cheek from interfering. Visibility is further restricted by saliva and by spraying water, which is applied to the surfaces being cut to minimize heating and to wash away cuttings. It is desirable to use as much cooling and lubricating water as possible to avoid the damage and pain of excessive heating, but the amount of spray must necessarily be restricted to permit visibility. Another disadvantage in present methods of dental cavity preparation resides in the need to install temporary fillings in order to cover sensitive cut surfaces, to prevent tooth drift and to protect the gums from food impaction while the permanent restorations are being prepared. Such temporary fillings require extra operator attention and, in addition, they tend to collect debris and can themselves irritate gingival tissue.

OBJECTS OF THE INVENTION

It is an object of this invention to provide an apparatus for machining a tooth wherein the dentist may actually perform his dental machining procedures on a model of the particular patient's jaw, thereby enabling the dentist to work in full view of the work, free of restrictions, when shaping teeth to desired configurations for receiving restorations.

It is a further object of this invention to provide an apparatus that improves accuracy by establishing a fixed relationship between the cutter and the teeth while machining on a model of the jaw and maintaining that same relationship while machining in the patient's mouth.

It is a further object of this invention to provide an apparatus that records the path of the cutter travel in the course of machining teeth on the model for later automatic duplication in the patient's mouth.

It is a further object of this invention to provide an apparatus that records the tilt of the cutter in the course of machining teeth on the model for later duplication in the mouth.

It is a further object of this invention to provide an apparatus for automatically machining teeth accurately with a selected, desirable taper on all sides.

It is a further object of this invention to provide an apparatus for machining teeth with a minimum amount of patient discomfort.

It is a further object of this invention to provide an apparatus for preparing teeth for fixed restorations, requiring fewer appointments and a minimum amount of a chair time.

It is a further object of this invention to provide an apparatus for indirect dental machining that will minimize operating time in the mouth by eliminating the need for intermittent stops to examine work in progress.

It is a further object of this invention to provide an apparatus for indirect dental machining that will drastically reduce the need for temporary fillings by eliminating the waiting period between tooth preparation and the placement of restorations.

It is a further object of this invention to provide an apparatus for machining teeth that will reduce stress in the dental environment by assuring accuracy without extra time.

It is a further object of this invention to provide an apparatus for machining a patient's tooth wherein the time and productivity of dental auxiliaries may be utilized to a greater extent than is presently feasible.

If is a further object of this invention to provide an apparatus for machining teeth, which in operation allows correction of cutting mistakes on such model before the natural teeth are cut.

It is a further object of this invention to provide an apparatus for machining teeth, which in operation reduces the possibility of unexpected pulp damage by first cutting model teeth where great accuracy is practical, so that accidental approaches to pulp locations becomes unlikely.

It is a further object of this invention to provide an apparatus for machining teeth, which minimizes patient discomfort, by automatically limiting cutting pressure and by supplying a copious flow of coolant.

Other objects and advantages of this invention will become apparent from the description to follow, particularly when read in conjunction with the accompanying drawings.

SUMMARY OF THE INVENTION

In carrying out this invention, there is provided a robotic device that is first anchored to a replica of the patient's jaw and later the same device or a duplicate thereof is anchored to the patient's jaw in precisely the same relative position. The device carriers a high-speed, air turbine-driven cutter. It is made to travel relative to the anchored base to any tooth and to then cut in three dimensions by employing at least three running at varying speeds, individually or in unison, to move the cutter vertically, side to side and in or out, the drives preferably being actuated by manipulation of one or more joysticks. Other drives are provided to maneuver the cutter above its roll and pitch axes as necessary. In addition, the anugular relationship between the device and the teeth may be established in installing the device, by tilting about both lateral and fore and aft axes.

In operation, an elevator motor controls the vertical motion of the cutting assembly with respect to the teeth; a lateral swing drive moves a sub-carriage to swing through a lateral arc; and an extender drive controls the extension and retraction of the cutter-carrying extender arm, all while a high-speed turbine rotates the cutter. In addition, a roll drive is employed to vary the angle of the cutter about a fore and aft axis, and a pitch drive controls the pitch of the turbine head.

At the patient's impression appointment, the gingival cuffs around teeth to be machined are retracted, and contacting surfaces of involved teeth are reduced to expose all pertinent included soft and hard tissues. Negative impressions are taken, in each case by use of a custom impression tray which is designed to rigidly support the apparatus of this invention, such tray being filled with a cream that sets to form a tough, accurate, non-shrinking, firm but elastic material.

Impression are poured in dental stone. After separating them from the models, windows are cut, and a sufficient amount of impression material is removed to expose the involved teeth when the tray is replaced on the mode. The cutter apparatus is attached to the tray and the assembly is replaced on the model. The cutter should start in "zero" location, i.e. in its central position with respect to lateral movement, fully retracted along its vertical path and fully withdrawn to the front of the mouth.

By manipulating the joystick, a shallow "check pit" is cut on the tray next to an involved tooth while this operation is recorded as a "reference program" in the computer memory.

The planned machining on model teeth is accomplished by manipulation of joysticks, while roll, pitch and cutter travel are stored as a program in the computer memory. While machining on the model, visibility is unobscured and the work can be viewed from all sides. When finished, the cutter is returned to "zero" location. Prior to machining the patient's natural teeth, restorations are fabricated.

The patient returns for a combined tooth machining and restoration placement sitting. The apparatus is attached to the impression tray as before. Accuracy of registration is checked by running the "check pit" program to ensure that the cutter returns precisely to the pit previously cut. Then, the assembly is placed over the patient's teeth. Natural teeth are cut under a copious supply of coolant, the cutter being guided by the computer at optimum cutting pressure, to duplicate the laboratory program without pause. Safety devices for stopping action are provided should problems arise, such as separation of the impression from the teeth. All necessary touch-up is completed, such as removal of remaining decay. When tested as satisfactory, the previously fabricated restorations are cemented.

BRIEF DESCRIPTION OF THE DRAWINGS

In the drawings:

FIG. 3 is a section view taken along line III—III of FIG. 2;

FIG. 4 is a section view taken along line IV—IV of FIG. 2;

FIG. 5 is a section view taken along line V—V of FIG. 2;

FIG. 6 is a vertical section view of a cutter arm embodiment; and

DESCRIPTION OF A PREFERRED EMBODIMENT

Figure 1:
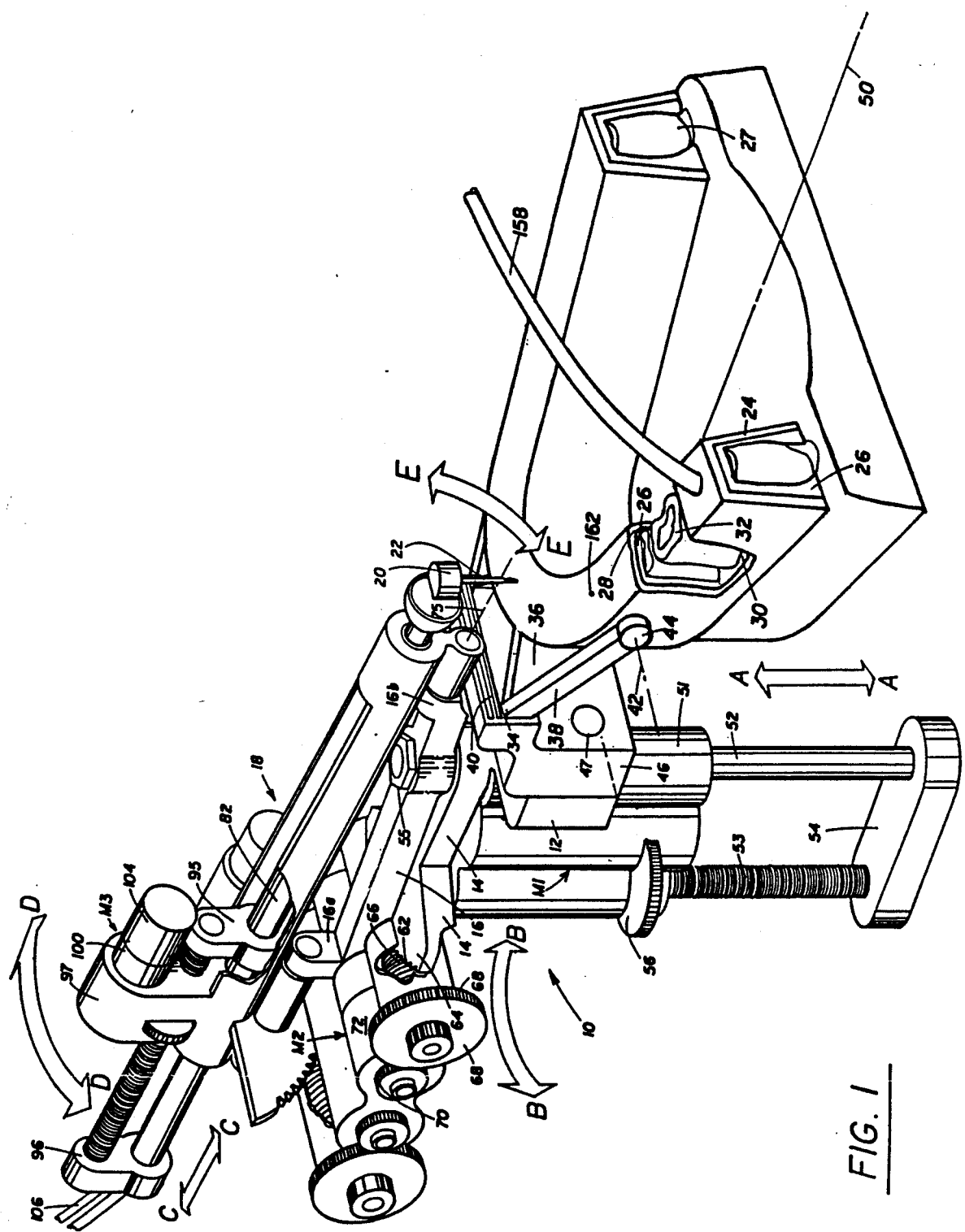
FIG. 1 is a view in perspective of a robot dental apparatus incorporating features of this invention.

Referring now to FIG. 1 with greater particularity, the robot dental apparatus 10 of this invention includes a base 12 on which, an elevator 14 is is mounted for vertical movement, as indicated by the arrow A—A. A sub-carriage 16 is mounted on the elevator for lateral, pivotal movement, as indicated by the arrow B—B. Mounted on the sub-carriage for extension and retraction movement, as indicated by the arrow C—C, is the cutter-carrying extender assembly 18, which carries an air-driven turbine 20 forwardly or rearwardly, i.e. in or out with respect to the jaw of a patient. As will hereafter be described, the extender assembly is mounted for movement about a roll axis 25, as indicated by the arrow D—D. A suitable, slightly tapered cutter or bur 22 is carried by the turbine 20 to be rotated at high speed in conventional fashion, and if desired, its attitude may be adjusted about its pitch axis, as indicated by the arrow E—E.

Anchoring The Base Member

Securing to the base member 12 in a manner to be described in greater detail, is a custom impression tray 24 carrying suitable, tough, elastic and and dimensionally stable dental impression material 26, which has previously been applied to the patient's jaw to form a negative impression of the patient's teeth. A positive image or casting 27 is made of the patient's jaw from the negative impression. Then, the same impression, or a duplicate second impression if desired, may be fit over the model 27, and, subsequently over the patient's own jaw to function as an anchor for the robot apparatus 10 of this invention. However, prior to fitting the impression tray 24 onto the robotic device 10, a portion of the tray 24 is cut away at 28 and sufficient impression material 26 is removed in the area 30 to form windows 30, which are adequate in size and number to fully expose the involved teeth 32 on which the dental work is to be performed, as well as the adjacent gum.

The impression tray 24 has a forwardly extending tab or handle 34 to provide a relatively stable support on the tray 24 for the dental machining apparatus 10. Toward this end the tab 34 is preferably made relatively rigid, as by means of reinforcing rigidifying ribs 36. The impression tray 24 is inserted into a yoke 38 with the tab 34 extending into a selected one of a series of notches or grooves 40 to give the impression tray 24 the desired forward tilt about the lateral axis 42, depending on the chosen angle of restoration insertion, considering, among other things, the angle of the involved tooth 32. When the proper angle is selected, the screws 44 are tightened to secure the impression tray 24 in place in the yoke 38.

The yoke 38 may be rigidly carried on a pivot block 46, which is attached to the base member 12 by suitable means, such as screws 47 (FIG. 4) which when loosened, enable the pivot block 46 to rotate partially on a pivot pin 49 about a fore and aft axis 50 to set the desired tilt of the impression tray 24 to compensate for the chosen direction of restoration insertion. Then, when the impression tray 24 is firmly secured on the patient's jaw or a model thereof, it will be disposed substantially horizontally, and the entire robot machining device 10 will be tilted about the axes 42 and 50 in accordance with the adjustment just described.

Vertical Movements Of The Elevator

The anchored base member 12 is provided with suitable linear bearings 51 to slidably receivce a smooth rod 52, on which the elevator 14 can move up and down, along arrow A—A, virtually without any lateral movement or vibration. A vertical threaded rod 53 is supported on the elevator 14, and the threaded rod 53 and main shaft 52 are secured firmly together by the interconnecting vertical stay 54. The elevator 14 moves with the threaded and slidable rods 53 and 52, and by reason of the its mounting on the radial bearing at 55, the pivotable sub-carriage 16 moves vertically with it.

Figure 2:
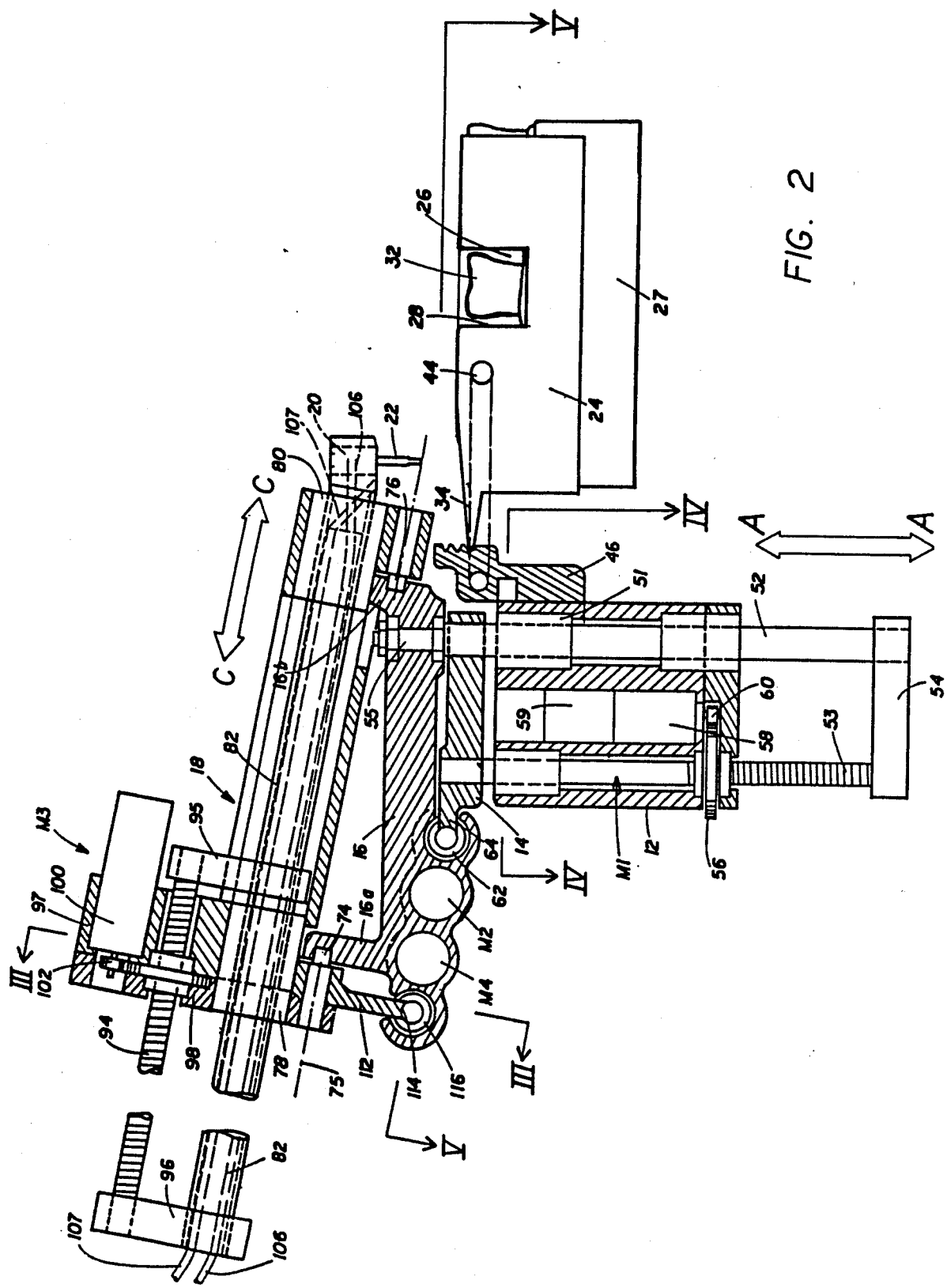
FIG. 2 is a vertical section view of the apparatus.

The base member 12 rotatably supports a gear 56 that is internally threaded to be received on the threaded rod 53. Hence, when the motor unit 58 (FIG. 2) of a standard motor-encoder unit M1 is energized, it drives a pinion 60 to rotate the internally threaded gear 56, causing it to drive the threaded rod 53 up or down on the base 12 and move the elevator 14 and sub-carriage 16 to a selected elevation. As the motor 58 rotates, an encoder 59 transmits signals to the computer, representative of the extent and timing of the rotation of that particular motor relative to other motors or drives, as will hereinafter be described.

Lateral Swinging Movement Of The Sub-Carriage

The sub-carriage 16 is mounted on the rotary bearing 55 for lateral swinging movmement relative to the elevator 14 and to the base member 12, about the axis of the rod 52. Gear teeth 62 are formed in an arcuate edge 64 on the elevator 14 (FIG. 5). The gear teeth 62 are engaged by a worn gear 66 which is rotatably carried in rotary bearings 67 formed on the pivoted sub-carriage 16. A gear 68 on the end of the worm gear 66 is driven by a pinion 70, which in turn is driven by the motor 72 of a standard gear driven motor-encoder M2. Hence, when the motor 72 is energized, the pinion 70 drives the gear 68 to rotate the worn ger 66 causing the sub-carriage 16 to pivot in the bearing 55 and move along an arcuate path traveling along the gear segment 62 through a predetermined arc B—B. This swings the sub-carriage 16 to effect lateral movement of the rotating cutter.

Of course, if desired, lateral movements of the carriage could be accomplished by means of a suitable rectilinear drive, whereby with the vertical drive along axis A—A and the extension and retraction along axis C—C, the tool 20 is driven through three orthogonal axes. However, the pivotal mounting or bearing 55 enables the tool 20 to be swung through a relatively wide angle to position the cutter 22 from side to side, while the lateral movements of the arm itself, in the area where it extends into the patient's mouth are relatively small for increased comfort. That is, the cutter can swing from molar to molar without requiring excessive distortion of the patient's mounth. As the motor 72 is driven, its encoder transmits signals representative of the extent and timing of travel to the computer.

Extending And Retracting Movements Of The Tool Carrying Arm

Supported on pivot mounts 16a and 16b on th lateral swing sub-carriage 16, is the extender assembly 18 including bearing mounts 78 and 80, which slidably receive a smooth, extender tube 82. The extender tube 82 is secured to a parallel threaded rod 94 by means of forward and rear extender stays 95 and 96. Rotatably mounted on an extender motor mount 97 is an extender annular gear 98, which is driven by another conventional, gear driven motor-encoder M3, with a motor 100, an output gear 102 (FIG. 2) and an encoder 104. As the motor 100 is driven, the encoder 104 transmits signals representative of the extent and timing of travel to the computer.

The turbine 20 is rotatably driven by a source of air from a hose 106 that extends through the tube 82. Return air from the turbine 20 is carried back through the tube 82 to exit to the atmosphere. Cooling water is delivered through a hose 107.

Adjusting Angle Of The Cutter About The Roll Axis Of The Extender Arm

The extender assembly 18 is carried on pivot pins 74 and 76 which are pivoted on the sub-carriage 16. Carried on the assembly 18 is a gear segment 112 (FIG. 3) with gear teeth 114 along an arcuate edge. Engaging the gear 114 is a worm gear 116, which is carried on a shaft 118 (FIG. 5) rotatably mounted in bearings 120, 121. Also carried on the shaft 118 is a gear 122 driven by a pinion 124, which, in turn, is driven by the motor portion 126 of a motor encoder M4. Hence, when the motor 100 is energized, the drive M-4 rotates the worm gear 116 to turn the arm 114 and pivot the extender assembly 18 about the axis 75 to dispose the cutter 122 at the desired angle along the arrow D—D. When the cutter 22 is disposed in its normal, vertical position, the axis 75 passes through the tip of the cutter so that the adjustment of the angle of the cutter about the roll axis does not displace the cutter tip from its cutting postion on the tooth. Even if the cutter tip is positioned slightly from the vertical, as will hereinafter be described, the displacement is so slight that a simple adjustment of the main drives, as previously described, will compensate quite readily.

The Pitch Adjustment Of The Cutter

Referring now to FIG. 6, the air turbine 20 may be carried on a mounting block 130 which is pivoted on the extender assembly 18 to pivot about axis 132 and along arrow E—E. An arm 134 extending from the mounting block 130 is threaded into an annular gear 136 which is engaged by a pinion 136 driven by the motor component 140 of the pitch control drive M5. Hence, when the drive M5 is actuated, the pinion 138 will drive the gear 136 to pivot the cutter to any selected position about its pitch axis from zero degrees to forty-five degrees. Such pitches up to forty-five degrees may be required for machining the lingual surfaces of the incisers.

The Drive Motors And Encoders For Feedback

Figure 7:
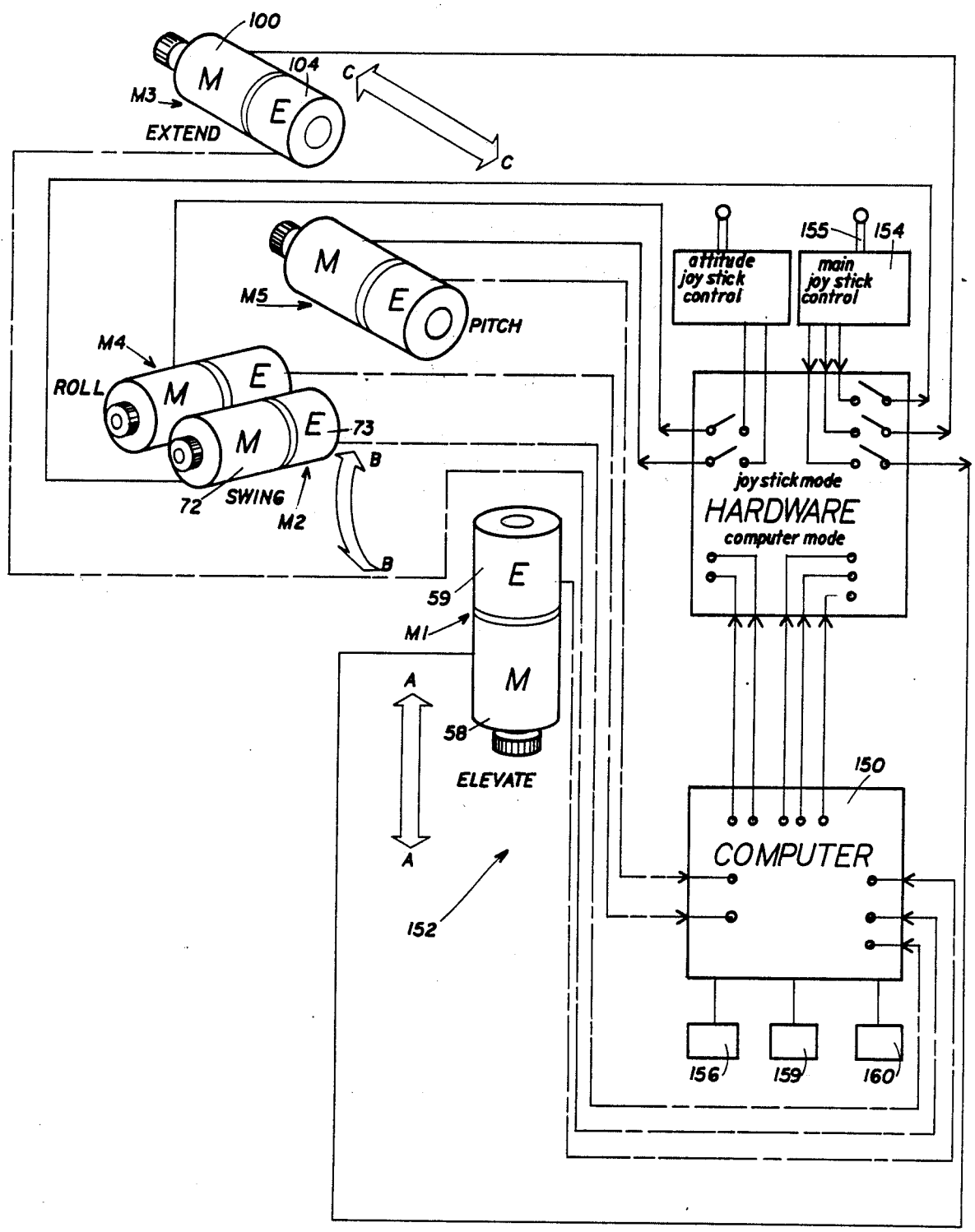
FIG. 7 is a wiring diagram of the apparatus.

Referring now particularly to FIG. 7, it will be noted that the drive M1 to raise and lower the elevator 14 along line A—A, the drive M2 to pivot and sub-carriage 16 laterally along are B—B, and the drive M3 to extend and retract the arm 18 along axis C—C all include rotary motors and encoders to feed signals to a computer 150 representative of the duration, timing and sequence at which each drive is energized. Standard, gear-drive motor-encoders M1, M2 and M3 may be employed to send to the computer signals representative of increments of movement of each motor.

When the dentist is working on the model teeth 32, the apparatus control 152 is switched to the joystick control mode 154 (FIG. 7) and signals are transmitted to the motors of motor-encoder units M1, M2 or M3, or any combination of such drives depending on the positions of joystick 155. As each motor is energized, a signal representative of the movement imparted by such motor is transmitted by the encoder 59, 73 or 104 to the computer 150.

It should be noted that, when the dentist is working on the model, he can move around the mode, or move th model itself as by placing it on a turntable (not shown) to improve his view and working angle. However the model may be positioned, the cutter 22 will be moved, and signals representative of such movement will be transmitted, relative to the base 12 and the impression tray 24. These same movements of the cutter 22 relative to the impression tray 24 are to be duplicated on the patient's own jaw.

When the same work is being performed in the mounth, as will be described, the apparatus control is switched to the computer control mode. Thereafter the motors 58, 72 and 100 are energized in response to, and for periods dictated by the computer 150. The computer operation can be stopped by appropriate safety switches, such as a vacuum switch 156 operated in the even that vacuum is lost in a line 158 (FIG. 1), which is in communication with the anchoring impression tray 24. When the anchoring tray is correctly applied to the jaw of the patient the tube 158 engages firmly against a tooth to shut off the outlet end and hold a vacuum. Then, should the tray 24 become dislodged, the vacuum will be lost and the switch will stop the computer 150, immediately interrupting any cutting action.

Also provided are manually operated safety switches 159 and 160 to be operated, respectively, by the patient and by the dentist.

Multi-Directional Movement Of The Tool

There have been described basically three directions of movement of the tool 20, i.e. laterally along arcuate arrow A—A, vertically along axis B—B and in and out of the patient's mouth along axis C—C. In addition, there are roll and pitch adjustments of the cutter 22 along arrows D—D and E—E, as delivered by additional attitude control drives M4 and M5 (FIGS. 3 to 6).

Operation Of The Apparatus

An impression is taken with tray 24 after retracting involved gingivae and reducing involved contact to expose relevant tooth anatomy. Cut surfaces are protected as required. The patient leaves.

In the laboratory, the impression is poured to produce the model 27 of the patient's jaw. The original impression or a new impression may be used as the anchor member 24. A tubular probe 158 is pushed through the impression material near the planned work to actuate a vacuum switch. Windows are cut through the impression tray 24, which functions as the anchor member and sufficient impression material is removed at 30 to clearly expose the subject teeth, such as tooth 32 when placed on the model 27. The apparatus 20 is attached to the anchor device 24 and the fore and aft tilt as well as the lateral tilt 44 ad 50 are adjusted in accordance with the chosen direction of the cutter. Tilt axes are recorded for future use.

The apparatus starts in the zero location which is in the elevated position of the carriage 14 along axis A—A, the center of the sub-carriage 16 along arc B—B and the fully retracted position of the arm 18 along extender axis C—C. This is the reference point from which all distances are transmitted and entered into the memory. The cutter 22 is moved near a subject tooth 32 where it machines a shallow depression in the tray called the test point 162. This is saved in the computer memory as the test point document. The tool is then moved to a subject tooth 32 to be machined to the desired profile. As the machining progresses, the dentist adjusts the attitude of the cutter where required, using the roll and pitch drives M4 and M5. All movements are saved in the computer memory as the cutting document. After machining is completed, the restorations (not shown) are fabricated and fit to the machined teeth of the model.

During the machining of the model tooth, the dentist's view is not obscured by saliva, spraying water or by the patient's tongue, cheek or other teeth. The model with apparatus 10 still in place can be moved for the convenience of the dentist since the cutter movements being transmitted to the computer are those made relative to the model and the impression tray 24, which is to be anchored thereto. With the apparatus and jaw model moved together, there is no relative movement.

When the restorations are ready, the patient returns for a second visit. Prior to seating of the impression on the natural teeth, the patient's program is loaded into the computer, the apparatus is mounted on the patient's impression tray, tilt axes are adjusted and the test point program is run. If runnning the test point document proves that the attachment of the apparatus to tray is in precisely the same position as it was on the model, the combined tray and apparatus is installed by anchoring the impression tray 24 to the natural teeth. Then, the cutting program is run.

Travel of the tool from test point 162 to the subject tooth, as well as from one tooth to another tooth if more than one is involved, is made at a rapid rate and without rotation of the cutting tool 22, and without spray.

During actual machining, water is supplied to the tooth and the cutter in generous supplies to ensure adequate cooling and sufficient lubrication, since the need for high visibility is not a factor.

During cutting movement a number of safety and comfort devices are incorporated. For example, as described, a vacuum tube 158 is closed off by contact with an adjacent tooth in the patient's mouth so that, should the anchor device become dislodged, the vacuum will be broken and the switch opened to interrupt the machining of the tooth.

Hand controlled safety switches 159 and 160 are available for operation by the patient and by the attendant so that should any discomfort be detected or should the attendant note anything wrong with the procedure, the machining may be interrupted by opening the appropriate switch.

When the tooth is completely machined, the previously prepared restoration may be installed and fitted as necessary.

While this invention has been described in conjunction with a preferred embodiment thereof, it is obvious that modifications and changes therein may be made by those skilled in the art to which it pertains without departing from the spirit and scope of this invention, as defined by the claims appended hereto.

What is claimed as invention is:

1. Apparatus for machining a tooth comprising:
an impression tray;
an elastic and dimensionally stable dental impression material in said tray;
said tray and impression material having been applied to a patient's jaw to form a negative impression thereof;
a positive model of said patient's jaw formed from a negative impression thereof;
a portion of said tray and impression material having been cut away so that when said negative impression is received over a patient's jaw or said positive model, a selected portion of a tooth to be machined is exposed;
a base member;

a rotatable cutter driving member mounted for movement on said base member in at least three degrees of motion;

means for firmly securing said impression tray to said base member;

said impression tray forming anchor means for selectively securing said base member in precisely corresponding positions on said patient's jaw or on said positive model;

recording means operative when said anchor means is secured to said positive mode to record movements of said cutter driving membe relative to said base member in cutting a tooth on said model; and duplicating means selectively actuated when said anchor means is secured to said patient's jaw to duplicate said recorded movements of said cutter driving member relative to said base member.

2. Apparatus for machining a tooth comprising:
an impression tray;
an elastic and dimensionally stable dental impression material in said tray;
said tray and impression material having been applied to a patient's jaw to form a negative impression thereof;
a positive model of said patient's jaw formed from a negative impression thereof;
a portion of said tray and impression material having been cut away so that when said negative impression is received over said patient's jaw or said positive model, a selected portion of a tooth to be machined is exposed;
a base member;
a cutter driving member mounted for movement on said base member in at least three degrees of motion;
first drive means for moving said driving member selectively in either vertical direction;
second drive means for moving said driving member on said base member selectively in either lateral direction;
third drive means for selectively extending or retracting said driving member;
means for firmly securing said impression tray to said base member ;
said impression tray forming anchor means or selectively securing said base member in precisely corresponding positions on said patient's jaw and on a said positive model;
means selectively operated when said anchor means is secured to said positive model for moving said cutter driving member in a selected path relative to said base member to machine a tooth on said positive model;
first, second and third signal-generating means for generating first, second and third signals proportionate to the extent of motion of said driving member in said vertical, lateral and extending direction, respectively; and
computer means for receiving and storing said signals in sequence and in time relationship to each other, said computer means being selectively actuated when said anchcor means is secured to said patient's jaw to deliver said first, second and third signals to said first, second and third drive means to move said tool in said selected path relative to said base member.

3. The tooth machining device defined by claim 2 including:

means for setting the tilt angle of said base member relative to said anchor means about a generally horizontal, transverse axis.

4. The tooth matching device defined by claim 2 including:
means for setting the tilt angle of said base member relative to said anchor means about a generally horizontal, fore and aft axis.

5. The tooth machining device defined by claim 2 including:
fourth drive means for partially rotating said driving member about a roll axis parallel to the direction in which driving member is moved by said third drive means;
fourth signal-generating means or generating fourth signals proportionate to the extent of rotation of said driving member about said roll axis;
said computer means being conditioned to receive and store said fourth signals in sequence and intmed relation to said first, second and third signals;
said computer means being selectively actuated when said anchor means is secured to said patient's jaw to deliver first, second, third and fourth signals to said first, second, third and fourth drive means to move said tool in said selected path relative to said base member.

6. The tooth machining device defined by claim 5 including:
fifth drive means for pivoting said driving member about a pitch axis transverse to the direction to which said driving member is moved by said third drive means; and
fifth signal-generating means for generating fifth signals proportionate to the extent of pivotal movement of said driving member about said pitch axis;
said computer means being conditioned to receive and store said fifth signals in sequence and in timed relation to said first, second, third and fourth signals, said computer means being selectively actuated when said anchor means is secured to said patient's jaw to deliver said first, second, third, fourth and fifth drive means to move said tool in said selected path relative to said base member.

7. The tooth machining device defined by claim 2 wherein said first drive means includes:
an elevator carrying said driving member ;
a generally vertical threaded rod on said base member to extend through said elevator; &1 an internally threaded, elevation adjustment nut receiving said threaded rod and rotatably mounted on said elevator: and
means for rotating said elevation adjustment nut.

8. The tooth machining device defined by claim 2 wherein said cutter driving member includes:
a sub-carriage mounted for pivotal movement on said elevator about a generally vertical axis to swing in both lateral directions; and
said second drive means includes;
an arcuate gear on said elevator disposed on an arc about said vertical axis;
a worm gear on said sub-carriage engaging said arcuate gear; and means for rotating said worm gear.

9. The tooth machining device defined by claim 8 wherein said third drive means includes:
a threaded rod carrying said cutter driving member extending generally forwardly through said sub-carriage;

an internally threaded arm extension adjustment nut receiving said threaded forwardly extending rod and rotatably mounted on said sub-carriage; threaded forwardly extending rod and rotatably mounted on said sub-carriage;

means for rotating said arm extension threaded nut.

10. The tooth matching device defined by claim 2 including:

safety switch means for interrupting delivery of said signals to said first, second and third drive means in the event said impression tray and impression becomes dislodged from said patient's teeth.

11. Apparatus for machining a tooth comprising:

a base member;

a cutter driving member mounted for movement on said base member in at least three degrees of motion;

first drive means for moving said driving member selectively in either verticl direction;

second drive means for moving said driving member on said base member selectively in either lateral direction;

third drive means for selectively extending or retracting said driving member;

anchor means for selectively securing said base member is precisely corresponding positions on a patient's jaw and on a model of said jaws;

means for setting the tilt angle of said base member relative to said anchor means about a generally horizontal axis;

means selectively operated when said anchor means is secured to said model for moving said cutter driving member in a selected path relative to said base member to machine a tooth on said model;

first, second and third signal-generating means for generating first, second and third signals proportionate to the extent of motion of said driving member in said vertical, lateral and extending direction, respectively; and computer means for receiving and storing said signals in sequence and in timed relationship to each other, said computer means being selectively actuated when said anchor means is secured to the patient's jaw to deliver said first, second and third signls to said first, second and third drive means to move said tool in said selected path relative to said base member.

12. The method of machining a tooth comprising the steps of:

providing a base member with a rotatable cutter mounted thereon for movement in at least three degrees of motion;

providing recording means operative to record movements of said cutter driving member relative to said base member;

providing duplicating drive means selectively actuated to duplicate said recorded movements of said cutter driving member relative to said base member;

providing a impression tray with an elastic and dimensionally stable dental impression material;

applying said tray and impression material to a patient's jaw to form a negative impression thereof;

using a negative impression of said patient's jaw to form a positive model thereof;

cutting a portion of said impression tray and negative impression away so that when applied to said patient's jaw or said positive model a chosen area thereof will be fully exposed;

securing said impression with negative impression to said base member;

applying said tray and negative impression to said positive model;

activating said rotatable cutter and moving same on said base to machine a model of a tooth;

applying said tray and negative impression to said patient's jaw; and actuating said duplicating means.

* * * * *